United States Patent [19]

Cohen et al.

[11] Patent Number: 4,609,743
[45] Date of Patent: Sep. 2, 1986

[54] METHOD FOR BREVICOMIN SYNTHESIS AND USE IN BEETLE CONTROL

[75] Inventors: Theodore Cohen; Mahadevan Bhupathy, both of Pittsburgh, Pa.

[73] Assignee: University of Pittsburgh, Pittsburgh, Pa.

[21] Appl. No.: 601,168

[22] Filed: Apr. 17, 1984

[51] Int. Cl.[4] .......................................... C07D 311/00
[52] U.S. Cl. .................................. 549/397; 549/355; 549/363
[58] Field of Search ...................... 549/397, 355, 363

[56] References Cited

U.S. PATENT DOCUMENTS

| | | | |
|---|---|---|---|
| 2,511,890 | 6/1950 | Whetstone | 549/355 |
| 2,511,891 | 6/1950 | Whetstone | 549/355 |
| 2,980,703 | 4/1961 | Dunlop | 549/355 |
| 3,228,075 | 8/1966 | Dietl | 424/278 X |
| 3,755,365 | 8/1973 | Fentiman, Jr. et al. | 549/355 |
| 3,755,563 | 8/1973 | Vité | 424/84 |

FOREIGN PATENT DOCUMENTS 646829 11/1950 United Kingdom .

OTHER PUBLICATIONS

Hoffman et al., Tetrahedron Letters, 23, 845 (1982).
Asami et al., Chemistry Letters, 93 (1983).
Cohen et al., Journ. Amer. Chem. Soc., 102 (1982), 6900.
Ferrier et al., J. Chem. Soc. Perkin Trans I, 1645 (1983).
Fuganti et al., Tetrahedron Letters, 3753 (1983).
Lipkowitz et al., 44, 486 (1979).
Cahiez et al., Tetrahedron Letters, 21, 1433 (1980).

Primary Examiner—Ethel G. Love
Attorney, Agent, or Firm—Arnold B. Silverman

[57] ABSTRACT

A process for the production of the beetle aggregation pheromone brevicomin comprising reacting acrolein dimer sequentially with ethyllithium, a methylating agent and aqueous protonic acid. In a modification of the process the acrolein dimer is reacted with ethyl Grignard reagent prior to reaction with an alkyllithium compound. The process includes distributing the brevicomin product to areas to be controlled for beetles.

36 Claims, 3 Drawing Figures

SINGLE FLASK METHOD

DOUBLE FLASK METHOD

METHOD FOR BREVICOMIN SYNTHESIS AND USE IN BEETLE CONTROL

BACKGROUND OF THE INVENTION

The invention described herein was made in the course of work under a grant or award from the Department of Health and Human Services.

FIELD OF THE INVENTION

This invention relates to a method for synthesizing brevicomin and to the use thereof in beetle control.

DESCRIPTION OF THE PRIOR ART

The exo and endo isomers of brevicomin are exuded by the female Western Pine Beetle (*Dendroctonus brevicomis*, LeConte) and the exo isomer is known to be a key component of the aggregation pheromone of this destructive pest. The endo isomer is a potent inhibitor of the aggregation behavior of the likewise destructive Southern Pine Beetle (*Dendroctonus frontalis*, Zimm). Both exo and endo brevicomin are released by the Mountain Pine Beetle (*Dendroctonus ponderosae*, Hopkins). The endo isomer is also released by the Southern Pine Beetle. The endo isomer is an antiaggregant not only in the Southern Pine Beetle, but also in the Mountain Pine Beetle. The exo isomer can behave as an attractant in *Temnochila chlorodia*, Mannerheim. Both isomers in racemic form (mixtures of the natural compounds with equal quantities of their mirror images) can be aggregation inhibitors for the Mountain Pine Beetle.

A number of methods are known for the synthesis of brevicomin and similar compounds. See U.S. Pat. Nos. 4,426,535, 2,511,890, 2,511,891, 2,980,703, 3,755,365, 3,755,563, 3,828,075 and British Pat. No. 646,829. See also "Short-Step Synthesis of Optically and Biologically Active Exo-Brevicomin", Y. Masaki et al., Tetahedran Letters, Vol. 23, No. 52, pp. 5553–5554, 1982 and Vite and Renwick, 58 Naturwissenschaften, page 418 (1971).

Other syntheses for the exo isomer include R. W. Hoffman and B. Kemper, Tetrahedron Letters, 23, 845 (1982); M. Asami and T. Mukaiyama, Chemistry Letters, 93 (1983); D. S. Matteson and K. M. Sadhu, J. Am. Chem. Soc., 105, 2077 (1983); R. J. Ferrier and P. Prasit, J. Chem. Soc. Perkin Transactions I, 1645 (1983); C. Fuganti, P. Grasselli, G. Pedrocchi-Fantoni, S. Servi, and C. Zirotti, Tetrahedron Letters 3753 (1983). A synthesis for a mixture of endo and exo isomers is shown in K. B. Lipkowitz, S. Scarpone, B. P. Mundy, and W. G. Bornmann, J. Org. Chem. 44, 486 (1979).

None of those references teaches the simplified method for synthesizing brevicomin disclosed herein wherein inexpensive acrolein dimer is reacted with an alkyllithium compound, a methylating agent and an aqueous acid.

SUMMARY OF THE INVENTION

The present invention provides an efficient method for synthesizing brevicomin in a single flask or vessel starting with acrolein dimer (2-formyl-2,3-dihydro-4H-pyran also called 3,4-Dihydro-2H-pyran-2-carboxaldehyde) and reacting said acrolein dimer sequentially with ethyllithium, a methylating agent and an aqueous protonic acid to produce a mixture of endo and exo brevicomins, predominating in the endo isomer.

A modification of the single flask method involves a double flask or vessel method in which the acrolein dimer is reacted with a Grignard reagent in first flask and the reaction product is then passed to a second flask where it is sequentially reacted with an alkyllithium compound, a methylating agent and aqueous protonic acid. This modification produces a mixture of endo and exo brevicomins with a slight excess of the exo isomer.

The brevicomin may be advantageously distributed in regions where beetle control is required in any known manner such as by localized placement in traps or by spraying.

It is an object of the present invention to provide an efficient method for the synthesis of brevicomin from an inexpensive starting material.

It is another object of this invention to provide a method for the production of a mixture of the endo and exo isomers of brevicomin predominating in the endo isomer.

It is a further object of this invention to provide a method for the production of a mixture of the endo and exo isomers of brevicomin containing an excess of the exo isomer.

It is still another object of this invention to provide a single flask method for the production of brevicomin.

It is another object of this invention to provide a modification of the single flask method for the production of brevicomin to change the proportion of the endo and exo isomers.

It is yet another object of this invention to use the brevicomin produced herein for insect control.

These and other objects of the invention will be more fully understood from the following description of the invention on reference to the illustrations appended hereto.

DESCRIPTION OF THE PREFERRED EMBODIMENTS

The present invention includes a one flask method for producing a mixture of the endo and exo isomers of brevicomin predominating in the endo isomer and a two flask method, which is a modification of the one flask method, for producing a mixture of the endo and exo isomers of brevicomin having a slight excess of the exo isomer. While the brevicomin so produced can be used for any purpose, it is particularly useful for controlling the aggregation behavior of the Western Pine Beetle, the Southern Pine Beetle and the Mountain Pine Beetle. Both isomers are exuded by the female Western Pine Beetle and the exo isomer is a key component in its aggregation pheromone. The endo isomer is a potent inhibitor of the aggregation behavior of the Southern Pine Beetle and the Mountain Pine Beetle.

Figure 1:
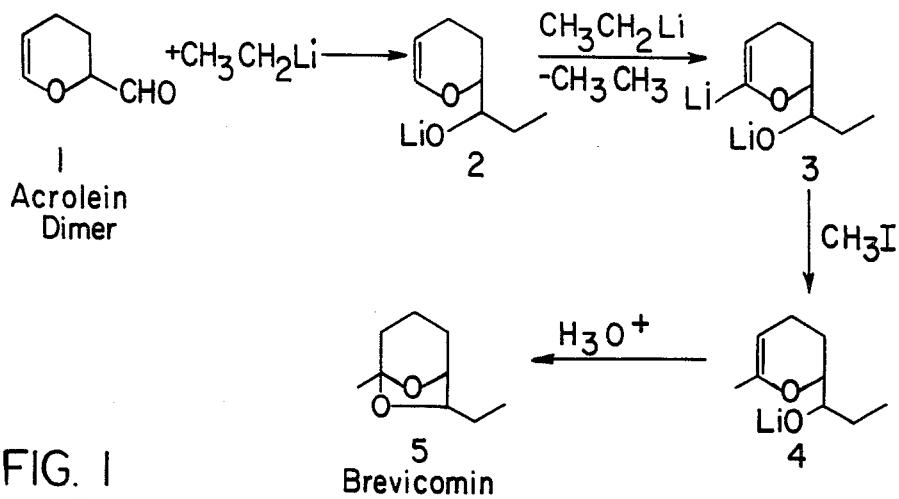
FIG. 1 presents a diagram indicating the sequential reactions and the structures of the nonisolated chemical entities produced in the one flask synthesis of brevicomin comprising predominantly the endo isomer.

FIG. 1 indicates the structures of the nonisolated chemical entities in the one flask synthesis of endo brevicomin. A key step is the conversion of Compound 2 to Compound 3 as this step allows the use of the inexpensive acrolein dimer (Compound 1) as the starting material and results in an extremely efficient synthesis. In the one-flask synthesis the ethyllithium reactant has two separate functions: it adds an ethyl group to the carbonyl (aldehyde) group, resulting in Compound 2, and it executes a proton-lithium exchange, resulting in Compound 3.

In the one flask method of FIG. 1 and Example 1 set forth hereinafter, at least 2.5 molar equivalents of ethyllithium must be used to avoid a considerable decrease in yield, while using more than 3 molar equivalents does not improve the yield. The same number of molar equivalents of tetramethylethylenediamine (TMEDA) as of ethyllithium should be used. Commercial ethyllithium can be used or the ethyllithium can be prepared from bromoethane as described in Example 3.

The presence of TMEDA provides high stereoselectivity (high ratio of endo to exo brevicomin). It acts as a chelating agent for lithium ions. Other complexing agents for lithium include hexamethylphosphoric triamide, crown ethers and cryptands.

Figure 3:
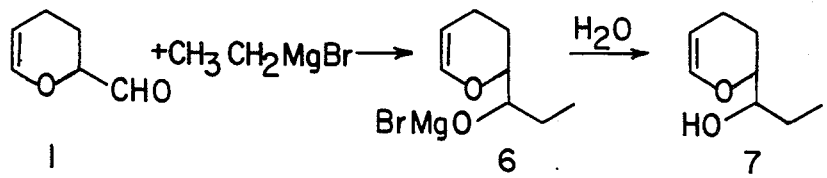
FIG. 3 presents a diagram indicating the sequential reactions and the structures of the nonisolated chemical entities produced in the two flask synthesis. The first line of FIG. 3 indicates reactions occurring in the first flask and the second line of FIG. 3 indicates reactions occurring in the second flask.
Figure 3:
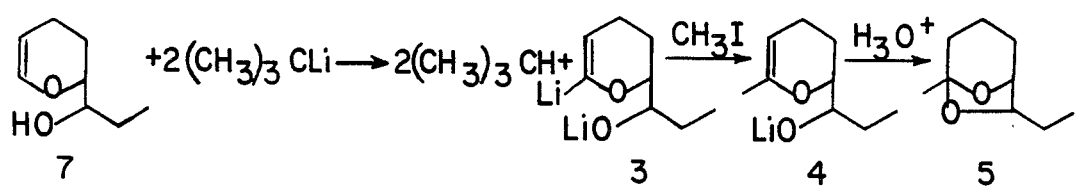

In FIG. 3 and Example 2, an ethyl Grignard reagent is substituted for ethyllithium in the aldehyde reaction step. In this modification, the proton-lithium exchange can be performed with any alkyllithium compound with the possible exception of methyllithium which may be too weak a base. Examples of suitable alkyllithiums are n-butyllithium, sec-butyllithium, tert-butyllithium, ethyllithium, etc. In the aldehyde reaction step, any nucleophilic ethylmetallic compound can be substituted for the Grignard reagent such as ethylsodium, ethylpotassium, ethylcalcium, ethylcadmium, ethylcopper and ethylaluminum compounds.

With regard to the methylation step in either the one-flask or two-flask procedure, any electrophilic methylating agent can be used. Examples are methyl bromide, dimethyl sulfate, methyl trifluoromethanesulfonate and methyl p-toluenesulfonate.

The acid addition step in both procedures can be performed with any moderately strong or strong protonic acid such as hydrobromic, sulfuric, trifluoroacetic or toluenesulfonic acid.

Wherever temperatures below 0° C. are specified in the following examples, the reactions can also be performed at room temperature or at temperatures up to about 40° C. with somewhat decreased yields.

EXAMPLE 1

The following one-flask synthesis resulted in a yield of 69 percent of a 4:1 mixture of the endo and exo isomers of brevicomin starting with commercially available agents.

Ethyllithium (three molar equivalents) was added to an ether solution containing one molar equivalent of acrolein dimer and three molar equivalents of tetramethylethylenediamine (TMEDA) at $-78°$ C. The solution was allowed to warm to 25° C. and was maintained at that temperature for at least 18 hours. It was then cooled to $-78°$ C. and methyl iodide (four molar equivalents) was added. The mixture was allowed to warm to 25° C. over 3 hours. It was equilibrated between water and ether and the organic phase was washed with two portions of 5% HCl solution and two of water. Concentration of the dried extract and distillation of the residue produced the isomeric brevicomins which were identified by comparison of their gas chromatographic, mass spectral, and 300 MHz $^1$H NMR characteristics (as a mixture and as the individual isomers obtained by partition chromatography) with reported values.

Referring to FIG. 1, the addition of the first equivalent of ethyllithium to Compound 1 produced the erythro and threo isomers of Compound 2. The remaining ethyllithium deprotonates the 2-position leading to Compound 3, which is converted to Compound 4 upon methylation. The acid induced ring closure of Compound 4 to form Compound 5 is then performed.

Figure 2:
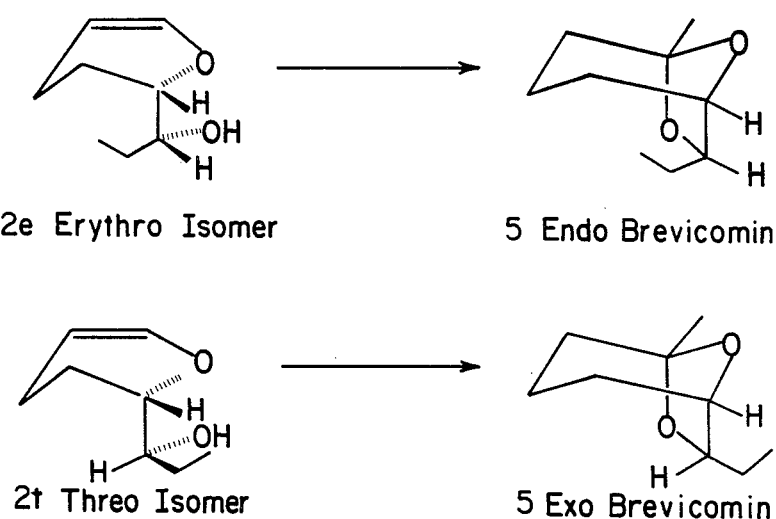
FIG. 2 illustrates the formation and structures of the endo and exo isomers of brevicomin.

Referring to FIG. 2, the erythro isomer of Compound 2 is shown as Compound 2e (Li=H) while the threo isomer of Compound 2 is shown as Compound 2t (Li=H). Compound 2e is the precursor of the endo brevicomin isomer of Compound 5 while Compound 2t is the precursor of the exo brevocomin isomer of Compound 5.

EXAMPLE 2

The following two-flask synthesis resulted in a yield of 49.6 percent (not optimized) of a 52:48 exo:endo mixture of the isomers of brevicomin. The reactions are illustrated in FIG. 3 wherein compounds similar to those of FIG. 1 have similar numerical designations.

To a solution of the acrolein dimer aldehyde (one equivalent) in anhydrous ether at 0° C. in a first flask, 1.3 equivalents of EtMgBr (3.1 molar in ether) was slowly added to form Compound 6. The mixture was then stirred at 25° C. for one hour. The reaction mixture was quenched with ice cold aqueous NH$_4$Cl solution and then equilibrated between ether and water. The organic layer was washed with water and dried with anhydrous MgSO$_4$. Evaporation of the solvent gave the mixture of alcohols 2e, Li=H and 2t, Li=H) as a pale yellow oil. The mixture of alcohols is generally indicated as Compound 7 and specifically shown as Compounds 2e and 2t in FIG. 2.

To the solution of the mixture of alcohols in anhydrous tetrahydrofuran (THF) at $-78°$ C. contained in a second flask, 3 equivalents of t-BuLi (1.48 M in pentane) was added. A canary yellow precipitate (t-BuLi-THF complex) was observed. After the addition was complete, the bath was replaced by an ice bath. The reaction mixture was stirred at 0° C. for one hour, diluted with anhydrous THF and recooled to $-78°$. C. Freshly distilled methyl iodide was added and the bath was allowed to warm to 0° C. The reaction mixture was stirred at 0° C. for 4 hours and then quenched with water. It was equilibrated between ether and water. The organic layer was treated twice with 5% HCl, once with water and then dried with anydrous MgSO4. Evaporation of the solvent gave the mixture of brevicomins. These were separated by flash chromatography (12% EtOAc in hexanes).

The ethyllithium used in Example 1 can be obtained commercially or it can be prepared from bromoethane by the following procedure.

EXAMPLE 3

To a stirring suspension of lithium wire containing 2 per cent sodium (3.2 mm diameter, 2.2 equivalents, Alfa Co.) in anhydrous ether at $-30°$ C., a solution of freshly distilled bromoethane (1 equivalent) in ether was added. The reaction mixture became cloudy. After the addition was complete, the mixture was stirred at 0° C. for two hours. The solution was then syringed out and stored under argon. It was estimated by Whitesides method. [G. M. Whitesides, C. P. Casey and J. K. Krieger, J. Am. Chem. Soc. 93, 19379 (1971)]. Yield 89%.

The brevicomin recovered from the above syntheses is a liquid. It may be employed undiluted or it may be admixed with a suitable solvent and distributed to control the dendroctonus beetles described above. The use may involve placing the brevicomin in a trap or by spraying or by evaporation via a wick, for example.

It will be apparent that the present invention is directed to the synthesis of brevicomin independently of or in connection with use for beetle control, or for any other use.

Whereas particular embodiments of the invention have been described for purpose of illustration, it will be appreciated by those skilled in the art that numerous variations of the details may be made without departing from the invention as described in the appended claims.

I claim:

1. A process for the production of brevicomin comprising reacting acrolein dimer sequentially with:
   (a) ethyllithium
   (b) a methylating agent, and
   (c) aqueous protonic acid, whereby a mixture of the endo and exo isomers of brevicomin will be produced.

2. The process of claim 1 wherein said ethyllithium is reacted in the presence of a complexing agent for lithium to increase the ratio of the endo to exo isomer of brevicomin.

3. The process of claim 2 wherein said complexing agent is tetramethylethylenediamine.

4. The process of claim 1 wherein about 2.5 to 3 molar equivalents of ethyllithium are reacted for each molar equivalent of acrolein dimer.

5. The process of claim 4 including about 3 molar equivalents of tetramethylethylenediamine in the ethyllithium reaction step.

6. The process of claim 1 wherein the acrolein dimer is in ether solution.

7. The process of claim 1 wherein the added ethyllithium is in ether solution.

8. The process of claim 1 wherein the solution is heated after the addition of ethyllithium.

9. The process of claim 1 wherein the solution is cooled prior to the addition of said methylating agent.

10. The process of claim 1 wherein said methylating agent is methyl iodide.

11. The process of claim 1 wherein the solution is allowed to warm after the addition of the methylating agent.

12. The process of claim 1 wherein said acid is aqueous HCl and the organic phase is washed with multiple portions of said acid.

13. The process of claim 1 wherein the product ratio of the endo to exo isomers of brevicomin is about 4:1.

14. The process of claim 1 wherein the yield of brevicomin is about 69 percent.

15. The process of claim 1 performed in a single vessel.

16. The process of claim 1 wherein the ethyllithium adds an ethyl group to the carbonyl group of the acrolein dimer to produce the erythro and threo isomers and also executes a proton-lithium exchange at the 2-position of the acrolein dimer.

17. The process of claim 3 wherein tetramethylethylenediamine and ethyllithium are added in about the same molar amounts.

18. The process of claim 10 wherein about 4 molar equivalents of methyl iodide are added per mole of acrolein dimer.

19. The process of claim 1 wherein said methylating agent is an electrophilic methylating agent selected from the group consisting of methyl bromide, dimethyl sulfate, methyl trifluoromethanesulfonate and methyl p-toluenesulfonate.

20. The process of claim 1 wherein said acid is a protonic acid selected from the group consisting of hydrobromic, sulfuric, trifluoroacetic and toluenesulfonic acids.

21. A process for the production of brevicomin comprising reacting acrolein dimer sequentially with:
   (a) an ethyl metallic compound,
   (b) alkyllithium,
   (c) a methylating agent, and
   (d) aqueous protonic acid, whereby a mixture of the endo and exo isomers of brevicomin will be produced.

22. The process of claim 21 wherein said alkyllithium is reacted in the presence of a complexing agent for lithium.

23. The process of claim 21 wherein said ethyl metallic compound adds an ethyl group to the carbonyl group of the acrolein dimer to produce the erythro and threo isomers and said alkyllithium executes a proton-lithium exchange at the 2-position of the acrolein dimer.

24. The process of claim 21 wherein said alkyllithium is selected from the group consisting of n-butyllithium, sec-butyllithium, tert-butyllithium and ethyllithium.

25. The process of claim 21 wherein said alkyllithium is tert-butyllithium.

26. The process of claim 21 wherein said alkyllithium is ethyllithium.

27. The process of claim 21 wherein said ethyl metallic compound is a Grignard reagent.

28. The process of claim 21 wherein said ethyl metallic compound is an ethyllithium compound.

29. The process of claim 21 wherein said ethyl metallic compound is selected from the group consisting of ethylsodium, ethylpotassium, ethylcalcium, ethylcadmium, ethylcopper and ethylaluminum compounds.

30. The process of claim 21 wherein said methylating agent is methyl iodide.

31. The process of claim 21 wherein said methylating agent is selected from the group consisting of methyl bromide, dimethyl sulfate, methyl trifluoromethanesulfonate and methyl p-toluenesulfonate.

32. The process of claim 21 wherein said aqueous protonic acid is an acid selected from the group consisting of hydrobromic, sulfuric, trifluoroacetic and toluenesulfonic acids.

33. The process of claim 21 wherein said acid is aqueous HCl.

34. The process of claim 21 wherein the brevicomin product includes the endo and exo isomers of brevicomin with an excess of the exo isomer.

35. The process of claim 21 wherein said ethyl metallic compound is ethyl magnesium bromide.

36. The process of claim 22 wherein said complexing agent is tetramethylethylenediamine.

* * * * *